United States Patent [19]

Wells et al.

[11] 4,195,179

[45] Mar. 25, 1980

[54] 5-(INDOL-3-YLMETHYLENE)-1,3-DIMETHYL-2-METHYLAMINO-4-IMIDAZOLIDINONE

[75] Inventors: Robert J. Wells; Peter T. Murphy, both of Cromer, Australia

[73] Assignee: Hoffmann-La Roche Inc., Nutley, N.J.

[21] Appl. No.: 830,242

[22] Filed: Sep. 2, 1977

[30] Foreign Application Priority Data

Sep. 7, 1976 [GB] United Kingdom ............... 36997/76

[51] Int. Cl.$^2$ .......................................... C07D 403/00
[52] U.S. Cl. ..................................... 542/444; 548/309
[58] Field of Search ................ 542/444; 548/309; 260/705

[56] References Cited

U.S. PATENT DOCUMENTS

| | | | |
|---|---|---|---|
| 1,849,576 | 3/1932 | Karrer | 260/705 X |
| 2,364,041 | 11/1944 | Stevens et al. | 260/705 X |
| 2,431,127 | 11/1947 | Kremers | 260/705 X |
| 2,833,771 | 5/1958 | Schwyzer et al. | 260/705 X |
| 3,441,563 | 4/1969 | Weisel et al. | 542/444 |
| 3,904,629 | 9/1975 | Failli | 548/309 |

FOREIGN PATENT DOCUMENTS 485113 12/1975 U.S.S.R. ................................. 548/309

OTHER PUBLICATIONS

Hollenbeak et al., Lloydia 40(5), pp. 479–481, (1977).
Kazlauskas et al., Tet. Letters, 1977, pp. 61–64.

Primary Examiner—Arthur P. Demers
Attorney, Agent, or Firm—Jon S. Saxe; George M. Gould; William G. Isgro

[57] ABSTRACT

5-(Indol-3-ylmethylene)-1,3-dimethyl-2-methylimino-4-imidazolidinone and its geometric isomers, prepared, inter alia, from indole-3-aldehyde and 1,3-dimethyl-2-methylimino-4-imidazolidinone, are described. The end products are useful as antidepressants.

3 Claims, No Drawings

5-(INDOL-3-YLMETHYLENE)-1,3-DIMETHYL-2-METHYLAMINO-4-IMIDAZOLIDINONE

DETAILED DESCRIPTION OF THE INVENTION

The invention relates to novel cyclic compounds, namely, 5-(indol-3-ylmethylene)-1,3-dimethyl-2-methylimino-4-imidazolidinone, its geometric isomers, and to a process for the preparation thereof.

The 5-(indol-3-ylmethylene)-1,3-dimethyl-2-methylimino-4-imidazolidinone can exist in isomeric forms, for example, the isomer E of the formula

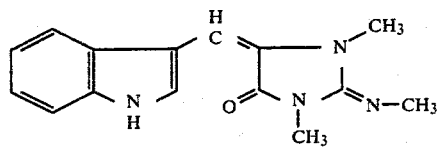

and the isomer Z of the formula

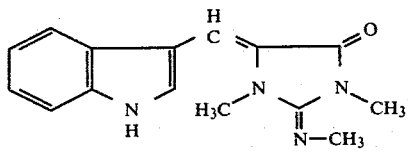

The compound of formula E-1 can be characterized as (E)-5-(indol-3-ylmethylene)-1,3-dimethyl-2-methylimino-4-imidazolidinone, and the compound of formula Z-1 can be characterized as (Z)-5-(indol-3-ylmethylene)-1,3-dimethyl-2-methylimino-4-imidazolidinone.

The compound of formula E-1, that is, (E)-5-(indol-3-ylmethylene)-1,3-dimethyl-2-methylimino-4-imidazolidinone, exists in low quantities in, and has recently been isolated by extraction from, a sponge belonging to the order Dictyoceratida, which can be collected on the Australian seacoasts. The substantially or essentially pure (E)-5-(indol-3-ylmethylene)-1,3-dimethyl-2-methylimino-4-imidazolidinone, that is, free from the other compounds contained in the sponge, thus constitutes a feature of the present invention. The 5-(indol-3-ylmethylene)-1,3-dimethyl-2-methylimino-4-imidazolidinone can be prepared in accordance with the invention by a process which comprises:

(a) condensing indole-3-aldehyde with 1,3-dimethyl-2-methylamino-4-imidazolidinone, or (b) reacting 5-(indol-3-ylmethylene)-1,3-dimethyl-2-imino-4-imidazolidinone with a methylating agent.

The imidazolidinone starting material utilized in embodiment (a) of this process has the formula

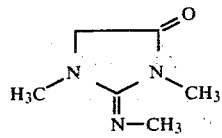

The E- and Z-isomers of the imidazolidinone starting materials utilized in embodiment (b) of this process have the formulas

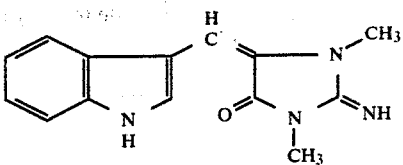

and

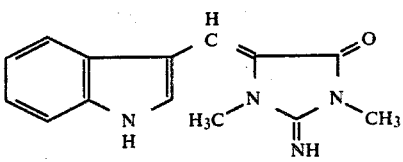

respectively.

The condensation of indole-3-aldehyde with the compound II, in accordance with embodiment (a) of the present process, can be carried out in a known manner, for example, by heating equimolar quantities of said starting materials in the presence of a condensation agent, at a temperature up to the reflux temperature of the reaction mixture, preferably at a temperature in the range of from about 50° to about 150° C. Exemplary of the condensation agents which can be utilized in the above reaction are aliphatic carboxylic acids and the alkali metal salts of such acids, for instance, acetic acid containing anhydrous sodium acetate and secondary or tertiary amines, such as piperidine, or mixtures thereof.

The methylation in accordance with embodiment (b) of the present process can be carried out in a known manner, for example, by heating 5-(indol-3-ylmethylene)-1,3-dimethyl-2-imino-4-imidazolidinone, with a methylating agent, such as methyl iodide, dimethylsulfate or methylated derivatives of dimethylsulfoxide, in an inert solvent, such as diethyl ether or ethanol, at a temperature up to the reflux temperature of the reaction mixture.

Substantially or essentially pure 5-(indol-3-ylmethylene)-1,3-dimethyl-2-imino-4-imidazolidinone is novel and forms also part of the invention.

5-(indol-3-ylmethylene)-1,3-dimethyl-2-methylimino-4-imidazolidinone and its geometric isomers have antidepressant activity. Such activity can be demonstrated in warm-blooded animals using standard procedure.

For example, the antagonism of tetrabenazine induced ptosis is demonstrated in male mice weighing 18–25 g. Groups of 10 mice each are administered tetrabenazine methanesulfonate at a dose of 100 mg/kg., one hour after oral administration of the test compound. One hour after tetrabenazine administration, each mouse is observed for the presence or absence of ptosis. An $ED_{50}$ value for the antagonism of tetrabenazine induced ptosis is then determined. (E)-5-(indol-3-ylmethylene)-1,3-dimethyl-2-methylimino-4-imidazolidinone was found to have an $ED_{50}$ of 5 mg/kg.

5-(Indol-3-ylmethylene)-1,3-dimethyl-2-methylimino-4-imidazolidinone and its geometric isomers have antidepressant properties qualitatively similar to compounds such as imipramine, harmaline and pargyline, which are known for their therapeutic uses and properties. In contradistinction to these known compounds, 5-(indol-3-ylmethylene)-1,3-dimethyl-2-methylimino-4-imidazolidinone and its geometric isomers have no anticholinergic or cardiovascular side effects. Furthermore, said known compounds are more toxic than 5-(indol-3-ylmethylene)-1,3-dimethyl-2- methylimino-4-imidazolidinone or geometric isomers. Refer, for example, to the following acute toxicity data, expressed in $LD_{50}$ mg/kg. in mice:

| Compounds | (E)-5-(indol-3-yl-methylene)-1,3-dimethyl-2-methylimino-4-imidazolidinone | imipramine | pargyline | harmaline |
|---|---|---|---|---|
| $LD_{50}$p.o. | 900 | 430 | 720 | 380 |
| $LD_{50}$i.p. | 670 | 125 | 390 | 120 |

5-(Indol-3-ylmethylene)-1,3-dimethyl-2-methylimino-4-imidazolidinone and its geometric isomers are useful for the treatment of depression. They can be utilized in medicine in the form of pharmaceutical preparations which contain one of them in combination with a compatible pharmaceutical carrier, for instance, an organic or inorganic inert carrier material suitable for enteral, for example, oral, or parenteral administration. Examples of such carrier materials are water, gelatin, lactose, starch, talc, magnesium stearate, gums, vegetable oils and petroleum jelly. The pharmaceutical preparations can be made up in a solid form, for example, as tablets, capsules, dragees or suppositories, or in a liquid form, for example, as solutions, emulsions or suspensions. The pharmaceutical preparations may be sterilized and/or may contain compatible adjuvants such as preservatives, stabilizing agents, flavoring agents, coloring agents, emulsifying agents, salts for varying the osmotic pressure or buffering agents.

Convenient pharmaceutical dosage forms contain about 1 to 100 mg. of 5-(indol-3-ylmethylene)-1,3-dimethyl-2-methylamino-4-imidazolidinone or its geometric isomers. Convenient oral dosages are in the range of about 0.1 mg/kg. per day to about 10 mg/kg. per day. Convenient parenteral dosages are in the range of about 0.01 mg/kg. per day to about 0.5 mg/kg. per day. However, the ranges mentioned can be extended upwards or downwards depending upon individual requirements.

The following Examples further illustrate the invention. All temperatures are stated in degrees Centigrade unless otherwise mentioned.

EXAMPLE 1

Preparation of (E)-5-(indol-3-ylmethylene)-1,3-dimethyl-2-methylimino-4-imidazolidinone 5 G. of 1,3-dimethyl-2-methylimino-4-imidazolidinone and 5 g. indole-3-aldehyde are refluxed in piperidine for 3 hours. The reaction mixture is poured into 250 ml. of water, stirred for 30 minutes, filtered, washed with water and dried. There are obtained 8.45 g. of (E)-5-(indol-3-ylmethylene)-1,3-dimethyl-2-methylimino-4-imidazolidinone.

The product recrystallizes from methanol in the form of yellow needles, mp 226.5°–228° C.

$^1$H n.m.r. (CD$_3$COOD) δ9.01 (1H, S), 7.78 (1H, m), 7.58 (1H, m), 7.30 (2H, m), 6.87 (1H, S), 3.33 (3H, S), 3.22 (3H, S), 3.13 (3H, S).

The following data are obtained by low resolution mass spectrometry:

$M^+$ 268 (61.9%), 253 (21.6%), 170 (23.7%), 169 (33.0%), 155 (base peak), 128 (25.3%), 101 (19.1%).

EXAMPLE 2

(a) The preparation of the starting material 255 mg of 1,3-dimethyl-2-imino-4-imidazolidinone hydriodide and 145 mg of indole-3-aldehyde are refluxed in 5 ml piperidine for 4 hours. After cooling, the reaction mixture is poured into 50 ml water. After stirring for 30 minutes the formed precipitate is filtered, washed with water and dried. There are obtained 205 mg of (E)-5-(indol-3-ylmethylene)-1,3-dimethyl-2-imino-4-imidazolidinone.

The product recrystallizes from methanol as fine, yellow needles, m.p. 231.8°–233.1° C.

(b) The process 500 mg of (E)-5-(indol-3-ylmethylene)-1,3-dimethyl-2-imino-4-imidazolidinone are refluxed in methanol for 24 hours with 425 mg of methyl iodide. The product is chromatographed on silica gel and alumina. There are obtained 107 mg of (E)-5-(indol-3-ylmethylene)-1,3-dimethyl-2-methylimino-4-imidazolidinone.

EXAMPLE 3

A mixture of 5.10 g of indole-3-carboxaldehyde, 5.64 g of dimethylcreatinine and 60 ml of piperidine was heated at reflux for 3 hrs, cooled to room temperature and poured into 350 ml of water. The precipitate was collected by filtration and dried to give 8.2 g of yellow solid, m.p. 241°–241.5°, which consisted of a 9:1 mixture of E- and Z-isomers. By heating a solution of the crude product in 2 l of methanol and 100 ml of piperidine at reflux for 2 hrs and removal of the solvents, a 1:1 mixture of E- and Z-isomers was obtained.

A one-gram sample of the above mixture (1:1 ratio of isomers) was digested with 20 ml of hot acetone and the soluble portion (565 mg) was applied directly to a column of 15 g of silica gel prepared in ethyl acetate. Elution was carried out with acetone collecting 20 ml fractions. Fractions 6, 7, and 8 were combined (144 mg) and crystallized from acetonitrile to afford 126 mg of (Z)-5-(indol-3-ylmethylene)-1,3-dimethyl-2-methylimino-4-imidazolidinone as a pale yellow solid, m.p. 241°–242°. The analytical sample was recrystallized from acetonitrile, m.p. 241°–242°. Mass spectrum m/e 268; UV (95% ethanol): 229 nm (ε22,400), 271 nm (9200); 365 nm (22,450); NMR (100 mHz, dimethylsulfoxide-d$_6$): δ7.67 (s, 1H, H-2), 6.75 (s, 0.94H, CH=C—CO, major) (attributed to the isomers of the C=N—CH$_3$), 6.48 (s, 0.06H, CH=CCO, minor) (attributed to the isomers of the C=N—CH$_3$).

Corresponding data for the E-isomer, which was isolated by crystallization of 9:1 mixture of isomers from methanol/methylene chloride: UV (95% ethanol): 232 nm (ε20,600), 276 nm (6950) 394 nm (22,600); NMR (100 mHz, dimethylsulfoxide-d$_6$): δ8.72 (broad, 1H, H-2); 6.47 (s, 0.67H, CH=C—CO, major) (attributed to the isomers of the C=N—CH$_3$), 6.30 (s, 0.33H, CH=C—CO, minor) (attributed to the isomers of the C=N—CH$_3$).

EXAMPLE 4

Tablets of the following composition are prepared in a conventional manner:

| | |
|---|---|
| (E)-5-(indol-3-ylmethylene)-1,3-dimethyl-2-methylimino-4-imidazolidinone | 50 mg |
| Lactose | 95 mg |

| | |
|---|---|
| -continued | |
| Maize starch | 100 mg |
| Talc | 4,5 mg |
| Magnesium stearate | 0,5 mg |
| Total weight | 250,0 mg |

We claim:

1. Essentially pure (E)-5-(indol-3-ylmethylene)-1,3-dimethyl-2-methylimino-4-imidazolidinone.

2. A process for the preparation of 5(indol-3-ylmethylene)-1,3-dimethyl-2-methylimino-4-imidazolidinone and its geometric isomers which comprises reacting 5-(indol-3-ylmethylene)-1,3-dimethyl-2-imino-4-imidazolidinone with a methylating agent, recovering 5-(indol-3-ylmethylene)-1,3-dimethyl-2-methylimino-4-imidazolidinone, and separating and recovering its geometric isomers.

3. A process in accordance with claim 2, wherein (E)-5-(indol-3-ylmethylene)-1,3-dimethyl-2-methylimino-4-imidazolidinone is recovered.

* * * * *